US010222336B2

(12) United States Patent
Kuo et al.

(10) Patent No.: US 10,222,336 B2
(45) Date of Patent: Mar. 5, 2019

(54) MULTIPLE SPECTRAL MEASUREMENT ACQUISITION APPARATUS AND THE METHODS OF USING SAME

(71) Applicant: HEWLETT-PACKARD DEVELOPMENT COMPANY, L.P., Houston, TX (US)

(72) Inventors: Huei Pei Kuo, Cupertino, CA (US); Zhiyong Li, Foster City, CA (US); Shih-Yuan Wang, Palo Alto, CA (US); Alexandre M Bratkovski, Mountain View, CA (US); Steven Barcelo, Palo Alto, CA (US); Ansoon Kim, Mountain View, CA (US); Gary Gibson, Palo Alto, CA (US); Mineo Yamakawa, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 10 days.

(21) Appl. No.: 14/414,206

(22) PCT Filed: Oct. 31, 2012

(86) PCT No.: PCT/US2012/062739
§ 371 (c)(1),
(2) Date: Jan. 12, 2015

(87) PCT Pub. No.: WO2014/070158
PCT Pub. Date: May 8, 2014

(65) Prior Publication Data
US 2015/0211998 A1 Jul. 30, 2015

(51) Int. Cl.
*G01N 21/65* (2006.01)
*G01N 21/64* (2006.01)

(52) U.S. Cl.
CPC ............ *G01N 21/65* (2013.01); *G01N 21/64* (2013.01); *G01N 2201/06113* (2013.01)

(58) Field of Classification Search
CPC ... G01N 21/65; G01N 21/64; G01J 2003/442; G01J 3/44
See application file for complete search history.

(56) References Cited

U.S. PATENT DOCUMENTS 4,505,586 A 3/1985 Tochigi et al.
5,455,673 A * 10/1995 Alsmeyer ................ G01J 3/44
356/301

(Continued)

FOREIGN PATENT DOCUMENTS

WO WO9808066 2/1998

OTHER PUBLICATIONS

Adany, P. et al., Tunable Excitation Source for Coherent Raman Spectroscopy Based on a Single Fiber Laser, Applied Physics Letters, Nov. 1, 2011, vol. 99, pp. 181112-1-181112-3.

(Continued)

*Primary Examiner* — Maurice Smith
(74) *Attorney, Agent, or Firm* — HP Inc. Patent Department

(57) ABSTRACT

A system includes an illumination source, a detector and a processor. The detector acquires spectral measurements of a sample under test under at least one varying condition. The processor processes the measurements to generate at least one spectral representation that includes Raman spectra and at least one spectral representation that includes non-Raman spectra.

16 Claims, 8 Drawing Sheets

(56) References Cited

U.S. PATENT DOCUMENTS

| | | | |
|---|---|---|---|
| 5,554,911 A * | 9/1996 | Nakayama | H01L 51/5036 313/503 |
| 6,264,331 B1 | 7/2001 | Sawai et al. | |
| 6,621,574 B1 * | 9/2003 | Forney | G01J 3/02 250/252.1 |
| 7,079,240 B2 | 7/2006 | Scherer et al. | |
| 7,564,547 B2 | 7/2009 | Yoo | |
| 7,880,882 B2 | 2/2011 | Jayaraman et al. | |
| 7,952,719 B2 | 5/2011 | Brennan, III | |
| 2002/0196817 A1 * | 12/2002 | Little | B81B 3/0021 372/20 |
| 2004/0125372 A1 | 7/2004 | Walla et al. | |
| 2005/0171436 A1 | 8/2005 | Clarke et al. | |
| 2006/0061761 A1 | 3/2006 | Li et al. | |
| 2006/0119843 A1 | 6/2006 | O'Connell | |
| 2006/0190216 A1 * | 8/2006 | Boysworth | G01J 3/28 702/179 |
| 2006/0197947 A1 | 9/2006 | Wang et al. | |
| 2008/0220512 A1 | 9/2008 | Koh et al. | |
| 2008/0310470 A1 | 12/2008 | Ooi et al. | |
| 2009/0097020 A1 * | 4/2009 | Treado | G01N 21/64 356/301 |
| 2009/0303487 A1 * | 12/2009 | Bond | G01N 21/39 356/437 |
| 2010/0315631 A1 * | 12/2010 | Zhou | G01J 3/10 356/301 |
| 2011/0085164 A1 | 4/2011 | Nelson et al. | |
| 2012/0035442 A1 | 2/2012 | Barman et al. | |
| 2012/0065490 A1 | 3/2012 | Zharov et al. | |
| 2012/0127468 A1 | 5/2012 | Bloch et al. | |
| 2012/0203086 A1 * | 8/2012 | Rorabaugh | A61B 3/1173 600/321 |

OTHER PUBLICATIONS

International Search Report and Written Opinion, dated Apr. 29, 2013. PCT Application No. PCT/US2012/062739.

Raman Scattering and Fluorescence, (Research Paper), Aug. 15, 2005.

* cited by examiner

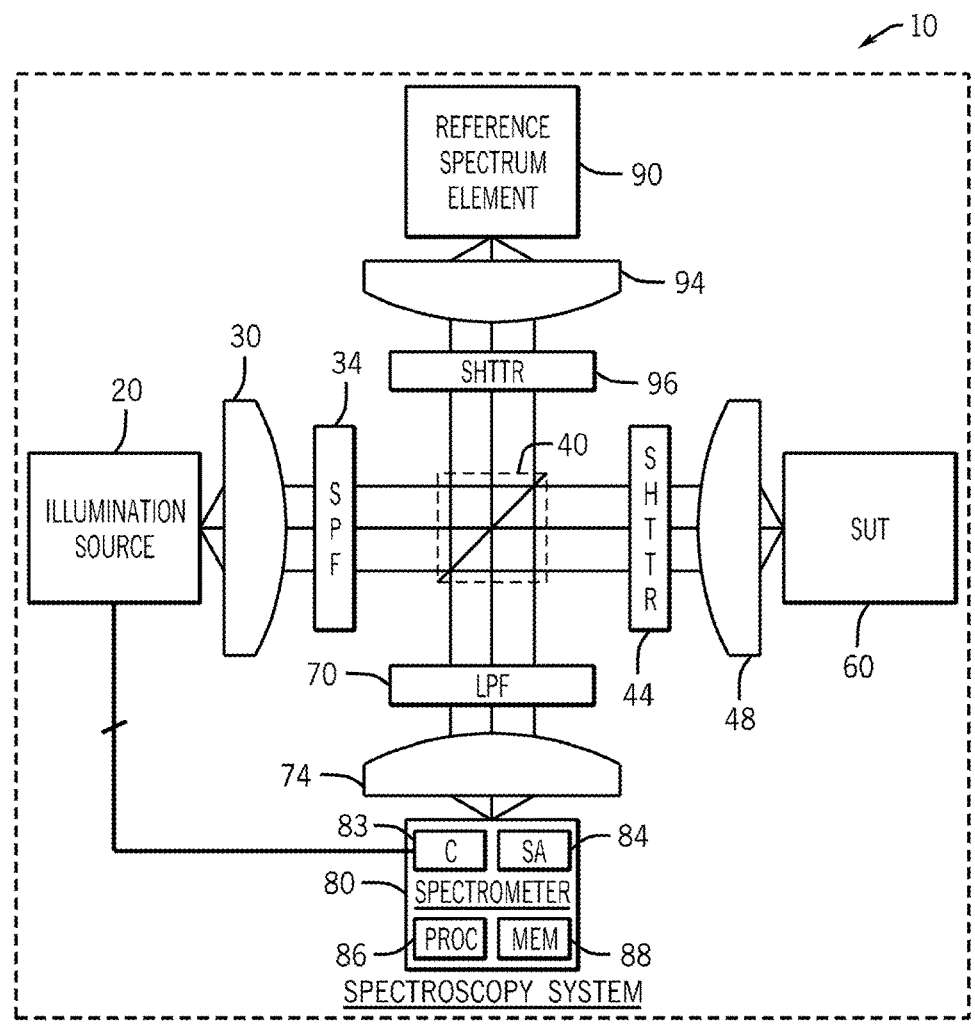
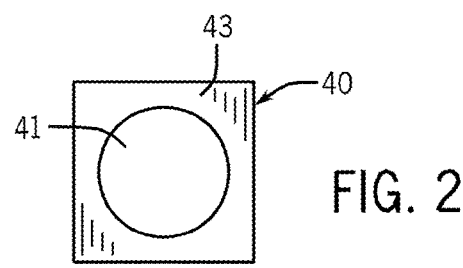
FIG. 1
FIG. 2

MULTIPLE SPECTRAL MEASUREMENT ACQUISITION APPARATUS AND THE METHODS OF USING SAME

BACKGROUND

Spectroscopy, which broadly refers to the interaction between energy and matter, may be used for such purposes as chemical and biological sensing. In a typical spectroscopy measurement, incident radiation (photons, for example) is directed to a particular analyte (i.e., a species, molecule, compound, biological or non-biological specimens, or, in general, matter being analyzed).

Raman spectroscopy refers to the study of vibrational, rotational and other specific modes of an analyte when incident photons scatter inelastically as a result of their interaction with the analyte. The scattered photons have a frequency that may be relatively low (called Stokes scattering), or relatively high (called anti-Stokes scattering), as compared to the frequency of the incident photons. The absorption of the incident photons and the resulting shifts in the wavelengths of the inelastically scattered photons as well as the relative peaks in the Raman emission are unique characteristics of the analyte. Hence, Raman spectroscopy has wide application for chemical and biological sensing, in particularly, in a portable system.

An analyte can also emit photons through various luminescence processes. In the fluorescence process (a relatively short-lived luminescence process, as compared to the phosphorescence process, which is luminescence from relatively long-lived states), the analyte emits photons as a result of absorbing incident photons by the molecules of the analyte. Similar to the Raman process, the wavelength of the re-emitted photons can be different from that of the incident photons. Stokes fluorescence is the re-emission of longer wavelength photons (lower frequency or energy). This energy difference is the Stokes shift. In the fluorescence process, an analyte can reemit photons with higher energy than the incident photon, and the energy difference is called an anti-Stokes shift (also called "up-conversion"). In the fluorescence and the other types of luminescence emission processes (e.g., bioluminescence and chemiluminescence processes), the absorption and the re-radiation (re-emission) of the photons together with the wavelength distribution of reemitted photons are unique characteristics of a particular molecular structure of the analyte.

BRIEF DESCRIPTION OF THE DRAWINGS

FIG. 1 is a semi-schematic view of a spectroscopy measurement system according to an example implementation.

FIG. 2 is a semi-schematic perspective view of a dichroic filter assembly of the spectroscopy measurement system of FIG. 1 according to an example implementation.

DETAILED DESCRIPTION

Figure 3:
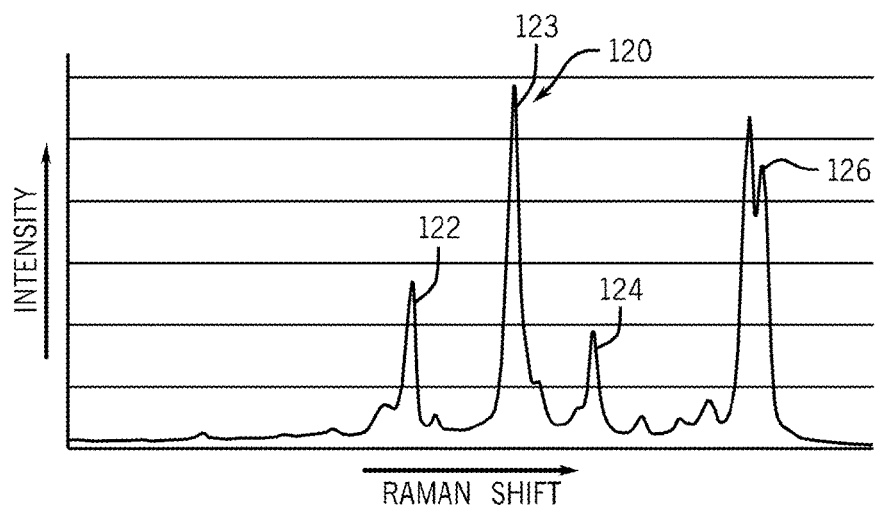
FIG. 3 is an illustration of a Raman spectrum emitted by a sample under test according to an example implementation.

The spectral energy, i.e. the spectrum, emitted by a given analyte (i.e., a species, molecule, compound, or biological or non-biological specimens, in general, mattering being analyzed) when subjected to incident electromagnetic or optical radiation depends on the composition of the analyte. In this manner, a spectroscopy measurement may contain one or more types of spectra intertwined together. For example, the spectra may include Raman photons, which are inelastically scattered, i.e., their wavelengths are shifted (up or down) by specific wavelengths relative to the wavelength of the incident photons. These shifts and the intensity distribution of the scattered photons also form a characteristic signature, or "fingerprint," of the analyte, the Raman spectrum. The spectra may also include luminescence photons, which occur when incident photons are absorbed and reemitted with shifted (up or down) wavelengths. With luminescence, the wavelengths of the reemitted photons and the intensity distribution, rather than the wavelength shifts, form another characteristic signature of the analyte, the luminescence spectrum. Fluorescence is a special case of photoluminescence.

In many cases, the co-existence of luminescence spectrum may undermine the quality of Raman spectrum for quantitative analysis of the analyte of interest. Techniques and systems are disclosed herein in accordance with example implementations to allow the reliable and convenient separation of Raman spectrum from non-Raman spectrum. More specifically, techniques and systems are disclosed herein for purposes of varying optical conditions (using different excitation wavelengths, for example) in connection with multiple spectroscopy measurements of an analyte (also called the "sample under test" herein) and processing these measurements to distinguish between Raman photons and photons emitted from other competing photon sources, such as luminescence spectra, for example. More specifically, techniques and systems are disclosed herein to differentiate, separate and reconstruct/recover the Raman spectra and the non-Raman spectra.

For example, if a given sample under test generates both Raman and fluorescence spectra, the system and techniques that are disclosed herein may be used to conduct spectroscopy measurements and process the measurements in a manner to derive separate representations of the Raman and fluorescence spectra conveniently and reliably. The identity of the sample under test may be determined based on the identified spectra. The techniques described here can enable the implementation of a compact system for sensor application. Moreover, as further described herein, the techniques and systems that are disclosed herein may be used in conjunction with a representation of reference spectra, which may be used to calibrate the spectroscopy measurement system.

It is thus noted that a particular compound that is in a given spectroscopy measurement may contain one or multiple molecules that are detectable using Raman, wavelength-shifted radiation from these molecules, whereas one or more other molecules of the compound may produce fluorescence and another luminescence emission simultaneously.

Referring to FIG. 1, as a more specific example, in accordance with example implementations that are disclosed herein, a spectroscopy measurement system 10 includes an illumination source 20 (a laser, for example), which produces radiation (incident photons, for example) that is incident upon a sample under test (SUT) 60 (i.e., an "analyte") for purposes of acquiring measurements of spectra from SUT 60.

The SUT 60 may be in proximity to or contain a surface to enhance and promote Raman scattering, in accordance with some implementations. In this manner, the often relatively inefficient Raman scattering process may be improved. This is called the surface enhanced Raman spectroscopy (SERS). As example, the Raman-scattering enhancing surface in SERS may be formed from one or more of rough metal surfaces; metal nanoparticles; various types of nano-antennas; nanostructures, such as nanofingers, nanowires coated with metal; black silicon coated with metal; as well as waveguiding structures. The SUT 60 may or may not be disposed near a SERS-based surface, in accordance with further implementations.

In accordance with example implementations, the spectroscopy measurement system 10 contains an optical subsystem to direct the incident radiation from the illumination source 20 to the SUT 60. The spectroscopy measurement system 10 further includes an optical subsystem to direct the resulting scattered light from the SUT 60 to a spectrometer 80, which, in accordance with example implementations, contains a sensor, or detector, to capture images (i.e., acquires spectral and or imagery data) and an analyzer to process the corresponding image data to separate and reconstruct the Raman, fluorescence and/or additional luminescence spectra.

More specifically, the illumination source 20 produces incident photons, which have relatively short wavelengths and pass through a lens 30 and a wavelength filter 34 of the spectroscopy measurement system 10 to allow the passage of at least a selected band of the emission from the illumination source 20 and block out spurious wavelength outside of the selected bands. The incident photons are further directed along an optical path that passes through a dichroic filter assembly 40, which, in turn, directs part of the incident light through an optical path that extends through a shutter 44 (when open), a lens 48 and to the SUT 60.

Various other implementations are contemplated and are within the scope of the appended claims. For example, in further implementations, the optical paths to the SUT 60 and a reference element 90 may be swapped. As another example, the filter will allow the passage of photons of relatively short wavelengths for anti-Stokes spectrometry.

The SUT 60 may exhibit fluorescence, other types of luminescence and/or Raman scattering, depending on its composition.

Figure 6:
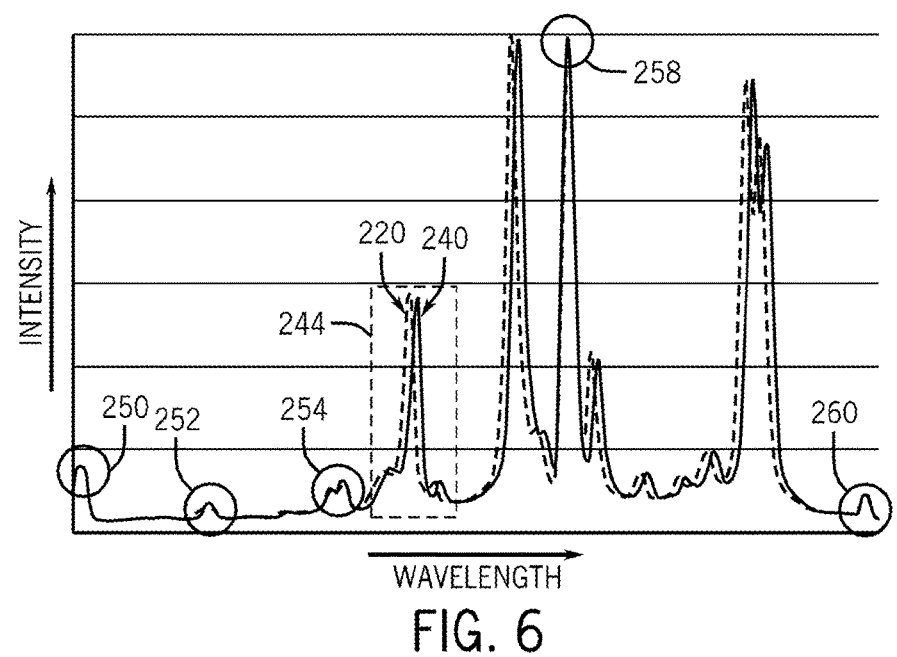
FIG. 6 depicts illustrations of composite spectra acquired in spectroscopy measurements of a sample under test performed using the spectroscopy measurement system of FIG. 1 and using different excitation source wavelengths according to an example implementation.

For Raman scattering, the interaction of the incident photons and the SUT 60 may cause a small fraction of the incident photons (approximately 1 in 10 million) to be scattered by atoms or molecules of the analyte, with the scattered photons having a frequency different from, and usually lower than, that of the incident photons. The intensity and the shift in frequency of the scattered photons are unique to the analyte and produce a characteristic "fingerprint" when the scattered photons are analyzed. The intensity and the wavelength distribution, i.e., the Raman spectra, of the inelastically scattered photons are the unique characteristics or the fingerprints of the analyte. Shown in FIG. 3 is an example Raman spectrum 120 when illuminated with an incident radiation of wavelength $\lambda_i$. The intensity of Raman scattered photons at wavelength $\lambda$ is plotted as a function of the wave number of the Raman shift, $(1/\lambda_i - 1/\lambda)$. In this representation, the peak distribution of the Raman spectrum remains relatively unchanged when the wavelength of the incident radiation, $\lambda_i$, is changed from $\lambda 1$ to $\lambda 2$. The locations of the analyte specific peaks, such as 122, 123, 124 and 126, have the same energy gain or loss independent of the energy (i.e. frequency/wavelength) of the incident photons. Raman spectra plotted in the conventional fashion, i.e., the intensity of the Raman scattered photons vs Raman shift in wavenumbers and thus, remain unchanged. As an alternative representation, the Raman spectrum is plotted against the wavelength. In this representation, the spectrum, however, may be shifted, as depicted in FIG. 6 and described in further details later.

The SUT 60 may also produce spectra through, for example, fluorescence, where the incident photons or other electromagnetic radiation is absorbed by the analyte and reemitted. In most cases, the emitted light has a longer wavelength, and therefore lower energy, than the absorbed radiation. However, when the absorbed electromagnetic radiation is highly coherent in a relatively short period, it is possible for one electron to absorb two photons; and this two photon absorption may lead to emission of radiation having a shorter wavelength than the absorbed radiation. The incident photon energy can be exactly same as the electron transition energy of a molecule, which may be termed "resonance fluorescence."

The intensity and the wavelengths of the luminescent photons, i.e., the luminescent spectra, form a characteristic signature of the analyte. Unlike the Raman spectra, the locations of the analyte specific luminescent peaks remain unchanged when the luminescent spectrum is plotted against the wavelength. Conversely, the locations of the luminescent peaks shift when plotted against the wave numbers $(1/\lambda_i - 1/\lambda)$.

Regardless of the composition of the light that results from the interaction of the incident radiation and the analyte, the resulting light is directed along an optical path passes back through the lens 48, the shutter 44 and to the dichroic filter assembly 40.

Due to the relatively long wavelength of the scattered light and the wavelength selectivity of the dichroic filter assembly 40, the assembly 40 directs the light along an optical path that passes through a filter 70 and, a lens 74 to an imaging, or sensing, array 84 (a CMOS/CCD sensor array, for example) of the spectrometer 80. It is noted that various features of the spectroscopy system 10 are omitted from FIG. 1 for purposes of clarity. For example, the spectrometer 80 may have additional components that are not shown in FIG. 1, such as gratings.

Referring to FIG. 2 in conjunction with FIG. 1, the dichroic filter assembly 40 may be formed from a dichroic material disk 41 that is surrounded by a specular reflector 43. The specular reflector 43 may be constructed from a reflective metal, such as polished aluminum, or gold. The incident and scattered light are directed by the disk 41 to the SUT 60 and the sensing array 84 of spectrometer 80, respectively. The specular reflector 43 also directs part of the incident light from the illumination source 20 through another optical arm of the spectroscopy measurement system 10 toward the reference spectrum element 90, in accordance with example implementations.

Figure 8A:
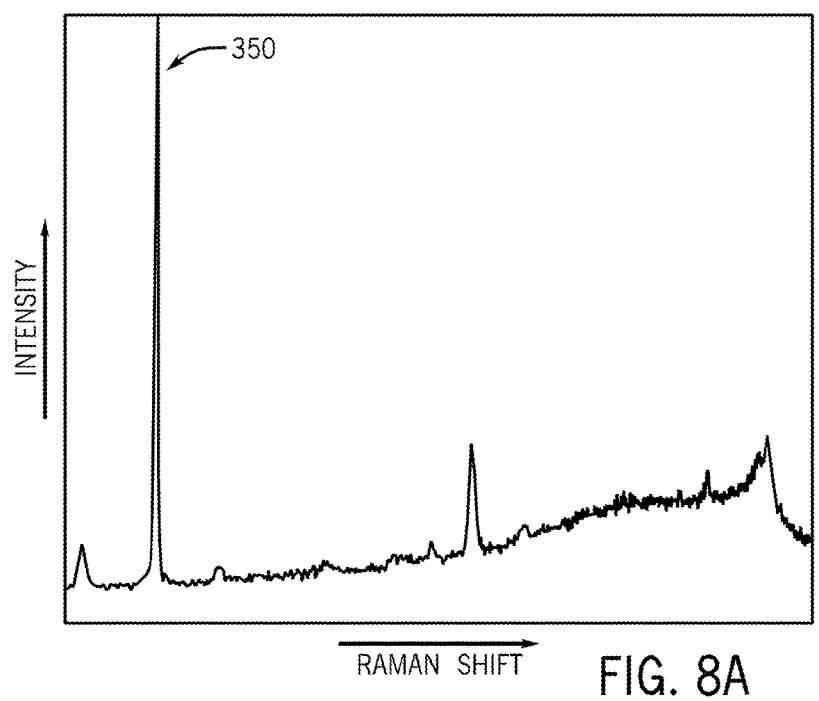
FIG. 8A is an illustration of a Raman-shift wavelength reference spectrum according to an example implementation.
Figure 8B:
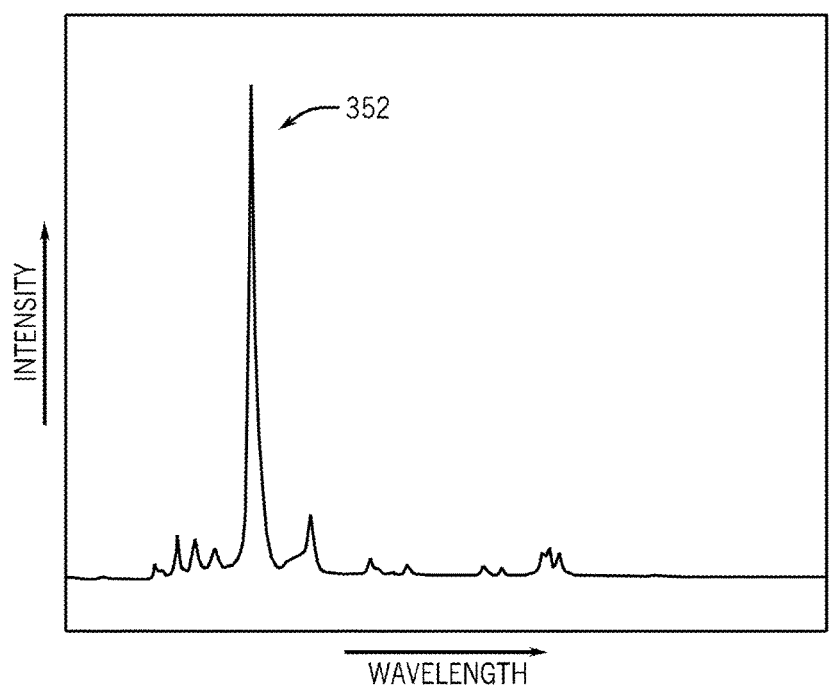
FIG. 8B is an illustration of a phosphor reference spectrum according to an example implementation.

More specifically, in accordance with an example implementation, light from the illumination source 20 is directed by the specular reflector 43 of the dichroic filter assembly 40 through a shutter 96 (when open), a lens 94 and to the reference spectrum element 90. As further disclosed herein, the reference spectrum element 90 may be a Raman shift reference element, which produces a reference spectrum that contains preferably sharp spectral peaks with precise and pre-calibrated shifts in wave numbers relative to the wavelength of the incident light. The reference spectrum element 90 may be an absolute wavelength reference that produces spectral energy distribution over a range of wavelengths. The spectral distribution contains preferably sharp spectral peaks located at precise and pre-calibrated wavelengths independent of the wavelength of the incident light. An example of the Raman shift is depicted in FIG. 8A and an example of a wavelength shift 352 is depicted in FIG. 8B. In further implementations, the reference element 90 may contain both a Raman wavelength shift reference and an absolute wavelength reference. Regardless of the implementation, however, the light from the reference element 90 is directed in an optical path through the lens 94, through the shutter 96 and to the dichroic filter assembly 40. The reference spectrum passes through the disk 41, through the long pass filter 70, through the lens 74 and to the sensing array 84 of the spectrometer 80.

In accordance with further implementations, the dichroic filter assembly 40 may be replaced by a beam splitter.

It is noted that in further implementations, one or multiple reference elements 90 may be disposed on a Raman-scattering enhancing surface in proximity of the SUT 60, and the spectroscopy measurement system 10 may not contain the above-described additional arm for communicating light with one or multiple reference elements 90. Thus, many variations are contemplated, which are within the scope of the appended claims.

Due to the above-described configuration of the spectroscopy measurement system 10, a given spectroscopy measurement acquired by the spectrometer 80 is a composite measurement, which contains one or more of fluorescence, luminescence, (incandescent) reference and Raman spectra.

Referring to FIG. 3 in conjunction with FIG. 1, as an example, the SUT 60 may contain at least one molecule that produces a Raman spectrum 120. The particular example Raman spectrum 120 depicted in FIG. 3 is the trans-1,2-bis (4-pyridyl) ethylene (BPE) molecule. The Raman spectrum 120 includes various spectral peaks, such as example spectral peaks 122, 124 and 126, whose respective wavelengths depend on the wavelength of the incident photon wavelength. It is noted that FIG. 3 does not depict the composite measurement acquired by the sensing array 84 for the example described herein, however.

Figure 4:
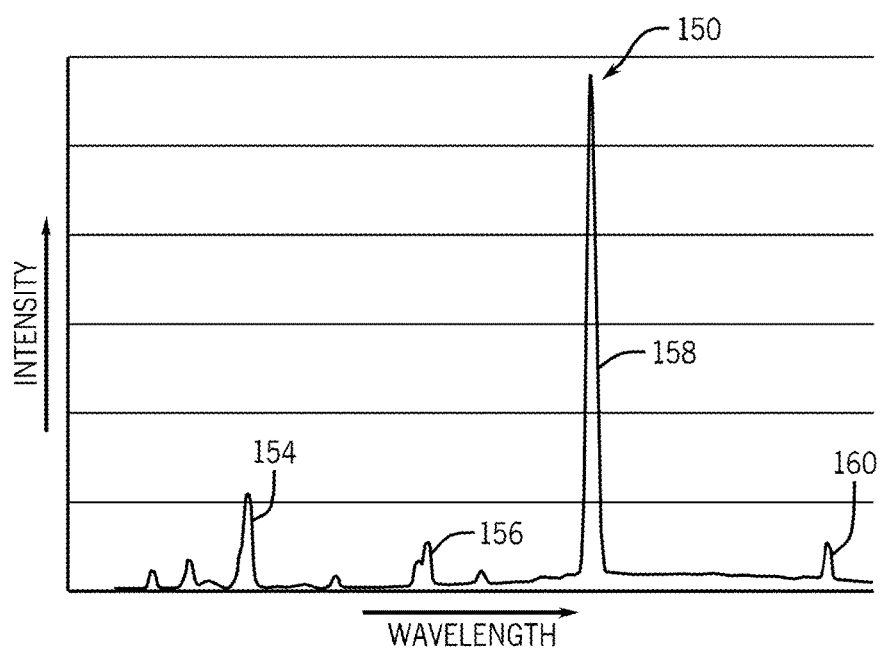
FIG. 4 is an illustration of a fluorescence spectrum according to an example implementation.

In this manner, FIG. 4 depicts an example fluorescence spectrum 150, which may be produced by a given reference material on or in the proximity of the SUT 60 or from reference spectrum element 90. The fluorescence spectrum 150 includes various spectral peaks 154, 156, 158 and 160, as shown in FIG. 4. These peaks 154, 156, 156, 158 and 160 are disposed at wavelengths, which unlike Raman spectra, do not change with the wavelength of the incident photons. As a specific example, the spectrum shown in FIG. 4 is a simplified, composite representation of the fluorescent spectrum of a red lamp phosphor and a mercury arc (peak 158).

Figure 5:
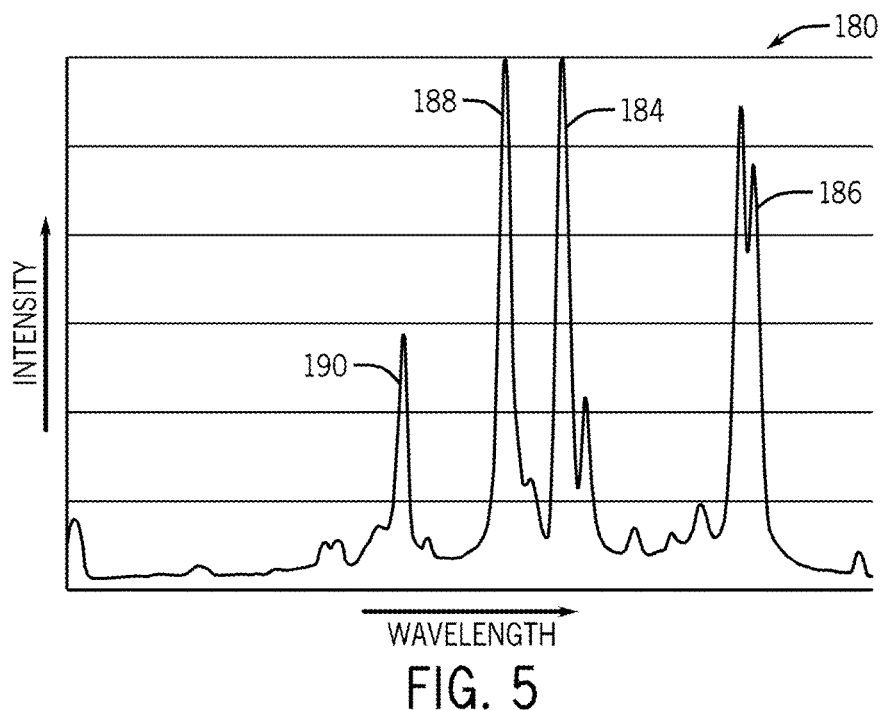
FIG. 5 is an illustration of a composite spectrum acquired by the spectroscopy measurement system of FIG. 1 according to an example implementation.

Referring to FIG. 5, the sensing array 84 senses a composite spectrum 180, which is a combination of the Raman spectrum 120 (FIG. 3), the fluorescence spectrum 150 (FIG. 4) and reference spectrum produced by element(s) 90. In example implementations, the intensity distribution vs wavelength of the reference peaks may be measured and calibrated beforehand and may be separated from the other fluorescent peaks. The composite spectrum 180 may further include fluorescence and/or luminescence background spectral energy attributable to the ambient environment of the spectroscopy measurement system 10. In example implementations, these types may be characterized beforehand and separated from the fluorescent spectral component of the SUT 60 and may be thus separated and reconstructed.

As disclosed herein, for purposes of discriminating between the above-different spectra, the spectroscopy measurement system 10 acquires multiple composite specific measurements and varies optical conditions in connection with these measurements, which allows the system 10 to discriminate the different spectra. For example, in some implementations, one or multiple inherent and/or controlled characteristics of the illumination source 20 vary among the measurements.

More specifically, in accordance with some implementations, the illumination source 20 varies the wavelength of the incident radiation so that the composite spectral measurements acquired by the spectrometer 80 are associated with different excitation wavelengths. As further disclosed herein, the different excitation wavelengths impart characteristics to the acquired measurements, which allows the Raman spectra to be discriminated from the fluorescence and/or luminescence spectra.

More specifically, in accordance with example implementations, the different excitation wavelengths introduce corresponding wavelength/wavenumber shifts in the Raman spectra among the composite measurements that are acquired by the spectrometer 80. However, the wavelengths of any fluorescence and/or luminescence spectra do not shift. Therefore, in accordance with example implementations, the spectrometer 80 uses this characteristic to separate the spectra. More specifically, FIG. 6 depicts an example in which two source excitation wavelengths were used at different times to produce two composite measurements of spectra 220 and 240, as captured by the sensing array 84 of the spectrometer 80.

In general, the Raman spectra-related portions of the spectra 220 and 240 are wavelength shifted versions relative to each other. In this manner, the Raman peaks, such as the peaks shown in illustrated portion 244, are separated in wavelength. The Raman spectra for the same species illuminated with different laser wavelengths $\lambda_{1,2}$ will be shifted with respect to each other to wavelengths $\lambda_{R1,2}$ that can be readily found from the relation:

$$\frac{1}{\lambda_{R1}} - \frac{1}{\lambda_{R2}} = \frac{1}{\lambda_1} - \frac{1}{\lambda_2}.$$

However, the fluorescence and/or luminescence spectra are not shifted in wavelength, but rather, remain at the same wavelength for the two spectra 220 and 240. This is illustrated in FIG. 6 by the peaks with circles 250, 252, 254, 258 and 260.

Techniques that are disclosed herein may be applied to process the composite measurements based on these characteristics to discriminate the Raman and fluorescence and/or luminescence spectra from each other.

Figure 7:
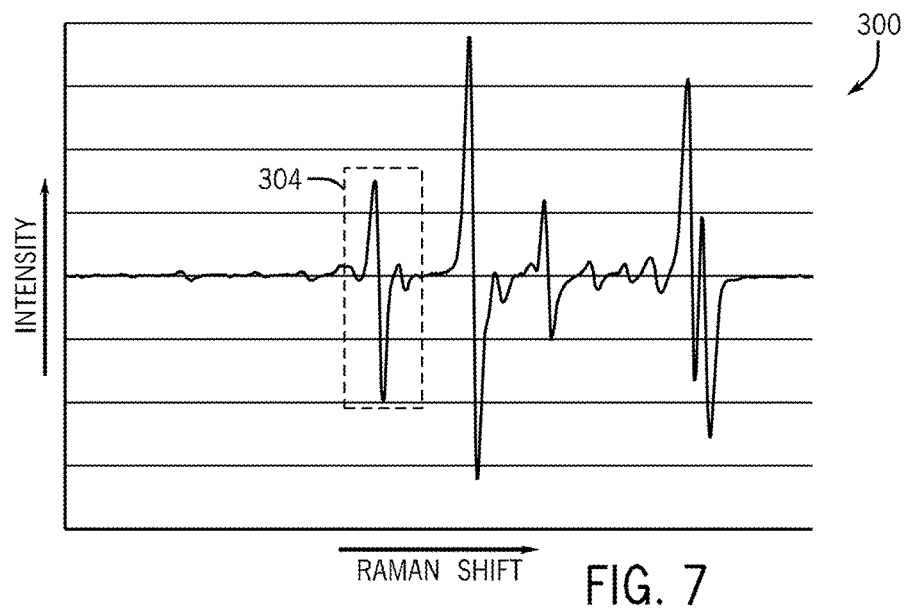
FIG. 7 is an illustration of a differential spectrum according to an example implementation.

For example, in accordance with example implementations, the spectrometer 80 processes two composite measurements associated with different excitation wavelengths to construct a differential spectrum, such as an example differential spectrum 300 that is depicted in FIG. 7, by subtracting the measurements, spectrum 220 and 240 in FIG. 6, from each other. With this subtraction, the fluorescence and/or luminescence spectra contained in the composite measurements are "zeroed," as depicted in FIG. 7. However, due to the wavelength shifting, the shifted Raman spectral peaks produce a nonzero differential spectra, such as exemplary spectra depicted in illustration portion 304 of FIG. 7. The Raman spectrum of FIG. 3 can be thus reconstructed, e.g., by integrating the differential spectrum 300, (for this example) with the fluorescence and/or luminescence spectra removed.

A representation of the fluorescence and/or luminescence spectra may be derived by subtracting the derived Raman spectra from the composite spectra.

Additional reconstruction techniques can be used. For example, the difference spectrum shown in FIG. 7 may be used as an alternative representation of the Raman spectrum shown in FIG. 3.

As yet another example, the SUT 60 may be illuminated with a switchable auxiliary source of excitation in addition to the illumination source 20. This would cause the intensity of (at least one of) the fluorescent peaks such as the peaks with circles 250, 252, 254, 258 and 260 to vary. The fluorescent peaks can thus be turned on and off if the auxiliary source is switched on and off.

Alternatively, in further example implementations, a representation of the fluorescence and/or luminescence spectra may be generated without first deriving a representation of the Raman spectra. In this manner, in accordance with an example implementation, one of two composite measurements may be shifted in wavelength relative to each other to align the corresponding Raman spectra peaks of the measurements and then the wavelength-shifted composite spectra measurement may be subtracted from the unshifted composite measurement. Similarly, the one of two composite measurements may be plotted as functions of Raman shift. In this manner the corresponding Raman spectra peaks of the measurements are aligned to facilitate the subsequent subtraction and reconstruction operation.

The spectrometer 80 may further incorporate at least one reference spectrum element. This allows the spectrometer to be calibrated accurately based on a prior knowledge of the reference spectra. For example, in accordance with some implementations, the reference spectrum element 90 may introduce a Raman wavelength shifted reference, such as a Raman reference 350 that is depicted in FIG. 8A. As an example, the Raman reference may be produced by silicon nanocones of the reference spectrum element 90, which introduces a wavenumber shift of ~520 cm$^{-1}$. This knowledge and other a priori knowledge of the components of the spectrometer 80 may be combined to facilitate the calibration of the spectrometer 80, in accordance with an example implementation.

In addition or in lieu of the Raman reference, the reference spectrum element 90 may be an absolute wavelength reference, in accordance with further implementations. In this regard, the reference spectrum element 90 may contain a phosphorous element, in accordance with some implementations.

As examples, the reference element 90 may contain one or more of the following compounds: a phosphor, such as Eu doped $Y_2O_3$ (see spectra 352 of FIG. 8B); BPE, Rhodamine 6G; and an upconversion phosphor, such as ytterbium and erbium doped in yttrium oxysulfide ($Y_2O_2S:Yb^{3+},Er^{3+}$) phosphors. Other compounds may be used, in accordance with further implementations.

The spectra of the reference element 90 can be concurrently or separately from the measurements of the spectra of the SUT. This is accomplished by opening and closing shutters 44 and 96 with appropriate timing sequences.

As noted earlier, the reference spectrum element may be incorporated as a component of SUT 60, in a further example implementation.

Figure 9:
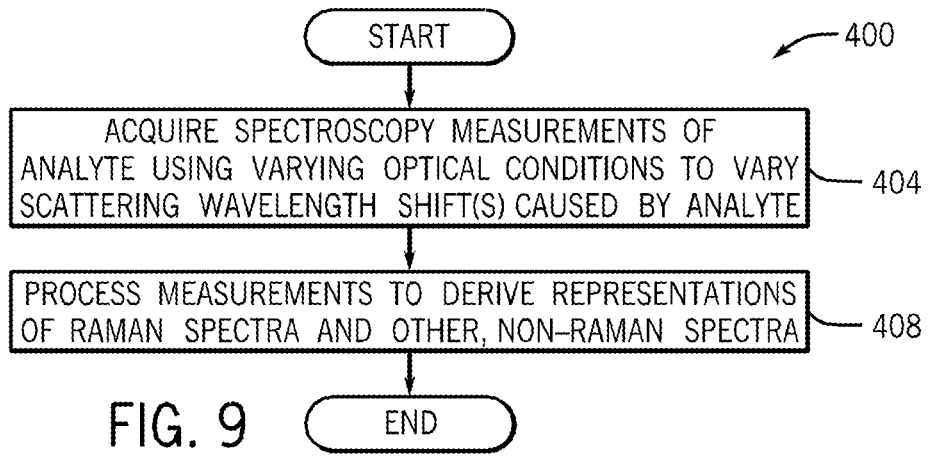
FIGS. 9 and 10 are flow diagrams depicting techniques to separate spectra acquired in spectroscopy measurements according to example implementations.

Referring to FIG. 9, thus, to summarize, in accordance with example implementations, a technique 400 includes acquiring (block 404) spectroscopy measurements of an analyte using varying optical conditions to vary one or multiple Raman shifts, which are caused by the analyte. The technique 400 includes processing (block 408) the measurements to derive representations of the resulting Raman spectra and other, non-Raman spectra (fluorescence spectra, photoluminescence spectra and so forth).

Referring back to FIG. 2, in accordance with example implementations, the spectrometer 80 may include a controller, which may, for example, control the sensing array 84 to acquire different "snapshots," or spectral images, associated with measurements that are acquired using different source excitation wavelengths. The controller may also control the illumination source 20 to vary optical conditions, as further described herein.

In an example implementation, the controller 83 may be formed at least in part by at least one processor 86 (a microprocessor, a microcontroller, a processing core, one or more processing cores, and so forth) of the spectrometer 80. The processor(s) 86 may further process data representing the composite spectra measurements to perform the technique 400 for purposes of constructing representations of the desired spectra. For this purpose, depending on the particular implementation, the processor(s) 86 may execute program instructions that are stored on non-transitory storage media, such as a semiconductor memory 88, magnetic storage, removable media, optical media, and so forth.

As a more specific example, the spectroscopy measurement system 10 may use a multimode laser for the illumination source 20, in accordance with example implementations.

In accordance with this example implementations, the measurements are acquired using data acquired using the laser when operating at its initial wavelength, and then the wavelength may shift by, e.g., approximately 0.1 nanometers (nm) by changing the temperature of the laser diode (via changing the power applied to the diode or changing the temperature of an oven or heating element used to heat the diode, as examples), as the gain spectrum shifts to a different wavelengths due to a change in the Fermi level due to the temperature change.

In this manner, when the multimode laser is initially powered up, or turned on, the laser shifts from an initial wavelength to a second wavelength by itself due to the laser junction heating up. Without waiting for the laser to stabilize, the spectroscopy measurement system 10 takes advantage of the initial instability of the laser to perform the measurements using different excitation wavelengths, i.e., using different wavelengths of the laser as the laser warms up.

Thus, the initial instability of the laser provides an automatic "tuning," in accordance with example implementations. It is noted that even with the laser being powered up for a considerable time, the laser may still transition between two to five wavelengths (as an example) due to the gain competition of the multiple modes near the peak of the gain spectrum.

Thus, varying the excitation wavelengths may be accomplished without temperature tuning and/or current tuning of the laser, in accordance with example implementations described below. The excitation wavelength may be varied using other techniques, in accordance with further implementations. For example, in accordance with further implementations, the power (current, for example) or bias point of the laser may be changed to cause the laser to emit different wavelengths. As another example, the laser temperature may be changed (through a heating element or a biasing point change, for example) to cause the laser to radiate different wavelengths. As another example, the laser may be operated in a pulsed mode of operation for purposes of modulating its wavelength. As another example, a plurality of excitation wavelength may be achieved by mechanically varying a length of a resonant cavity of a laser used for the illumination source 20. Thus, many variations are contemplated, which are within the scope of the appended claims.

Figure 10:
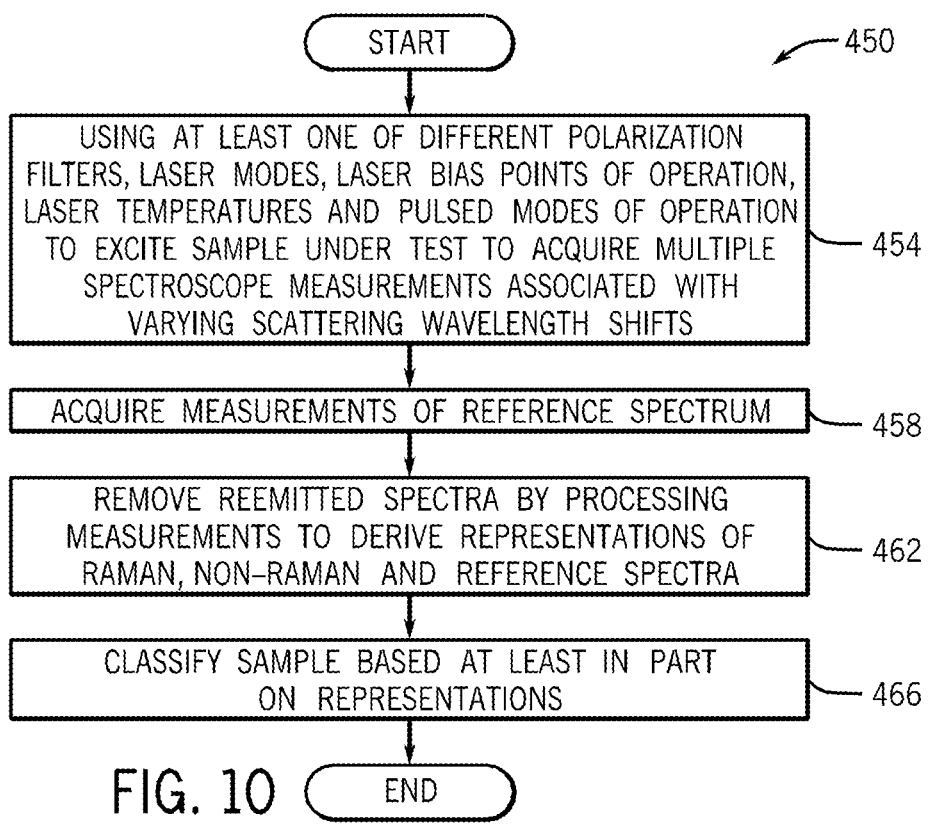

To summarize, FIG. 10 depicts an example technique 450 that may be used by the spectroscopy measurement system 10, in accordance with example implementations. Pursuant to the technique 450, the spectroscopy measurement system 10 performs (block 454) measurements using at least one of different laser modes, different laser bias points of operation, different laser temperatures and a pulse mode of operation to illuminate a sample under test with different excitation wavelengths. The measurements are then processed, pursuant to block 462, to derive representations of scattered and reemitted spectra. The sample may then be classified, pursuant to block 466, based at least in part on the representations.

Figure 11:
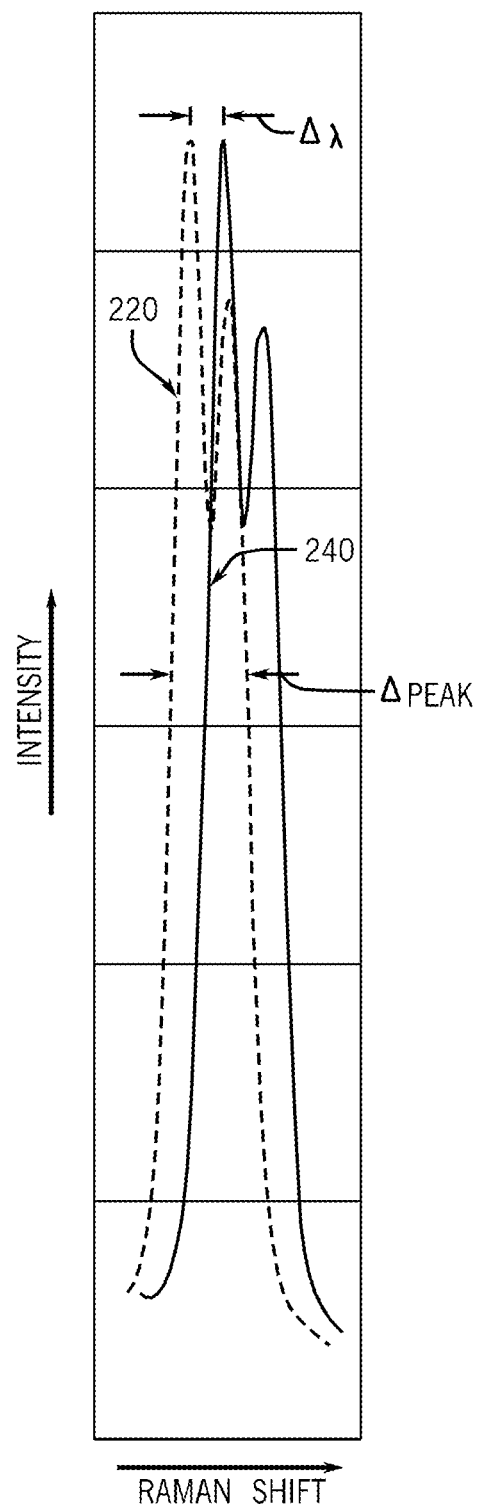
FIG. 11 is an illustration of a relationship between a wavelength shift and a Raman spectral peak width according to an example implementation.

Referring to FIG. 11, in accordance with example implementations, a given Raman wavelength shift (called "$\Delta\lambda$" herein) controls the resulting spectral energy that appears in the differencing spectrum and represents the Raman spectral peaks. In this regard, for a given Raman spectral peak full-width-at-half-maximum (FWHM) width (called "$\Delta_{PEAK}$" herein), the $\Delta\lambda$ wavelength shift controls the resulting intensity in the differencing spectrum. In this manner, for a given spectral $\Delta_{PEAK}$ width, a $\Delta\lambda$ wavelength shift that is too large or too small may result in reduced corresponding spectral energy in the differencing spectrum. Therefore, in accordance with example implementations, the $\Delta\lambda$ wavelength shifts are regulated to selectively target the Raman spectral peaks for purposes of optimizing the resulting spectra energy in the differencing spectrum, i.e., optimizing the integrated portions of the differencing spectrum, which corresponding to the Raman spectral peaks.

As a more specific example, in accordance with example implementations, the $\Delta\lambda$ wavelength shift is selected based on one or more targeted Raman spectral peaks so that the $\Delta\lambda$ wavelength shift is approximately one $\Delta_{PEAK}$ spectral width of the targeted peak(s). Because the widths of the Raman spectral peaks may vary for a given Raman spectrum, in accordance with example implementations, a plurality of $\Delta\lambda$ wavelength shifts may be used.

For example, a given Raman spectrum may contain three primary spectral peaks of substantially varying widths; and for this example, four excitation wavelengths may be used (i.e., three differencing wavelengths) for purposes of optimizing the resulting difference spectrum for each of these peaks. The results are then combined to produce a composite differencing spectrum/Raman spectrum.

Figure 12:
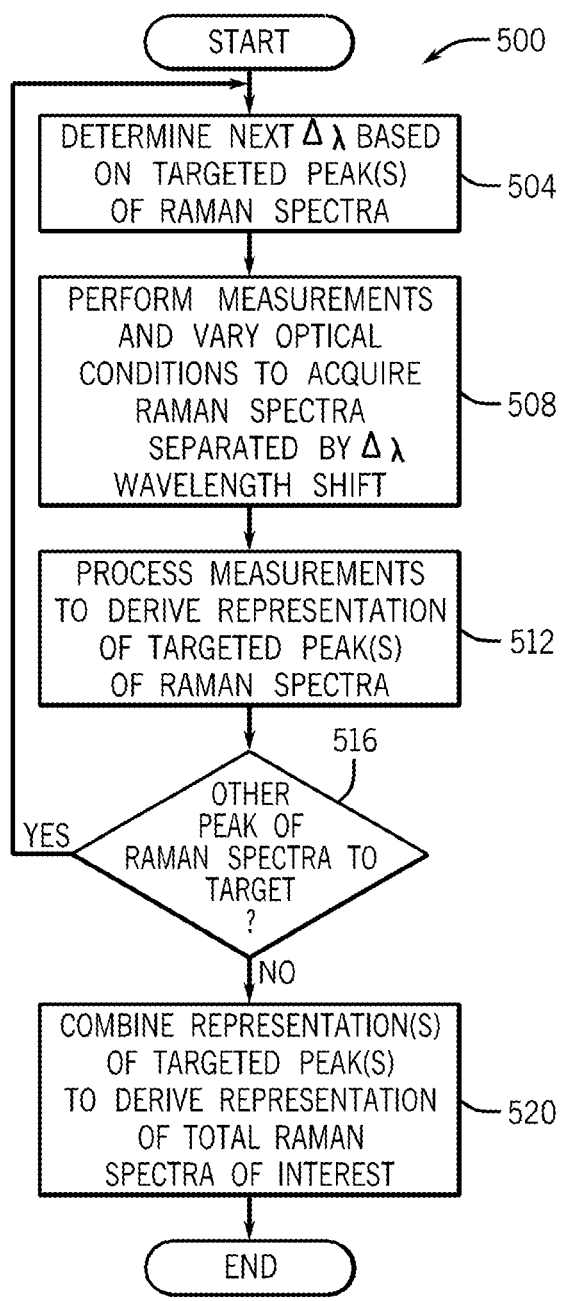
FIG. 12 is a flow diagram depicting a technique to use varying excitation wavelengths targeted at different Raman spectral peak widths to derive a representation of a Raman spectrum according to an example implementation.

More specifically, referring to FIG. 12, a technique 500 in accordance with an example implementation includes determining (block 504) the next $\Delta\lambda$ wavelength shift based on one or multiple targeted Raman spectral peaks. Measurements are then performed and optical conditions are varied to acquire Raman spectra separated by the $\Delta\lambda$ wavelength shift, pursuant to block 508. The resulting measurements may be then be used to derive a representation of the targeted Raman spectral peak(s). If a determination is made (decision block 516) that one or multiple other Raman spectral peaks are to be targeted, then the technique 500 includes determining the next $\Delta\lambda$ wavelength shift, performing the corresponding measurements and processing of the measurements, pursuant to blocks 504 and 508 and 512. When the measurements are complete, the representations may be combined, pursuant to block 520, to derive a representation of the total Raman spectrum of interest.

Other variations are contemplated and are within the scope of the appended claims. As examples, in accordance with further implementations, the optical conditions may be varied by varying one or more of the following: an illumination angle, a collection angle, an illumination amplitude, an auxiliary illumination source and an optical modulation.

While a limited number of examples have been disclosed herein, those skilled in the art, having the benefit of this disclosure, will appreciate numerous modifications and variations therefrom. It is intended that the appended claims cover all such modifications and variations.

What is claimed is:
1. An apparatus comprising:
a reference element;
a laser to illuminate the reference element and a sample under test with at least one varying optical condition;
a detector to acquire spectral measurements of the sample under test under the at least one varying optical condition;
light interacting elements to:
concurrently communicate light from the laser to the sample under test and to the reference element;
concurrently communicate light reflected from the sample under test to the detector and light reflected from the reference element to the detector, wherein the light interacting elements comprise a dichroic material disc surrounded by a specular reflector, wherein the detector acquires a spectral measurement comprising a spectrum composite based upon the light from the laser that is reflected from the sample under test and the light from the laser that is reflected from the reference element; and
a processor to process the measurements, including the spectrum composite, to discriminate Raman spectra from non-Raman spectra in the spectrum composite based upon the spectral measurements of the sample under test under the at least one varying optical condition and to generate a spectral representation of the spectrum composite based upon the discriminating, the spectral representation including the Raman spectra and excluding the non-Raman spectra.

2. The apparatus of claim 1, wherein the at least one varying optical condition comprises a varying wavelength of light output by the laser and illuminating the sample under test.

3. The apparatus of claim 1, wherein the laser has an adjustable resonant cavity, wherein the resonant cavity has a first length to provide a first exciting wavelength and a second length, different than the first length, to provide a second excitation wavelength, the first wavelength and the second wavelength both being applied during the acquiring of the spectral measurements of the sample pursuant to a single test.

4. The apparatus of claim 1, wherein the apparatus is adapted to perform at least one of the following to vary the excitation wavelengths:
  generate the excitation wavelengths using different modes of the laser;
  generate the excitation wavelengths by operating the laser at a different voltage or current;
  generate the excitation wavelengths by operating the laser at different temperatures; and
  generate the excitation wavelengths by operating the laser in a pulsed mode of operation.

5. The apparatus of claim 1, wherein the laser comprises a single laser and wherein the spectrum composite is based upon light from the single laser incident upon the sample under test and reflected from the sample under test.

6. The apparatus of claim 1 further comprising a reference element comprising a Raman scattering enhancing surface in proximity to the sample under test.

7. The apparatus of claim 1, wherein the non-Raman spectra comprises at least one spectra selected from a group of non-Raman spectra consisting of: fluorescence spectra, luminescence spectra and incandescent spectra.

8. The apparatus of claim 1, wherein the reference element contains a compound selected from a group of compounds consisting of: a phosphor; BPE, Rhodamine 6G; and an upconversion phosphor.

9. The apparatus of claim 1, wherein the reference element comprises a Raman shift reference element having a spectral distribution containing spectral peaks located at pre-calibrated wavelengths independent of a wavelength of incident light.

10. The apparatus of claim 1, wherein the reference element comprises a Raman wavelength shift reference and an absolute wavelength reference.

11. An apparatus comprising:
  an optical detector to acquire data indicative of a plurality of spectral measurements of an analyte, one of the spectral measurements comprising a spectrum composite comprising both Raman spectra and non-Raman spectra;
  an optical system of light outputting or interacting elements to vary optical conditions under which the plurality of spectral measurements are acquired from the analyte, wherein the optical system comprises an illumination source comprising a laser, the laser having an adjustable resonant cavity, wherein the resonant cavity has a first length to provide a first exciting wavelength and a second length, different than the first length, to provide a second excitation wavelength, the first wavelength and the second wavelength both being applied during the acquiring of the plurality of spectral measurement from the analyte pursuant to a single test;
  wherein the light interacting elements are to:
  concurrently communicate light from the laser to the analyte and to a reference element;
  concurrently communicate light reflected from the sample under test to the optical detector and light reflected from the reference element to the optical detector, wherein the light interacting elements comprise a dichroic material disc surrounded by a specular reflector, wherein the detector acquires a spectral measurement comprising a spectrum composite based upon the light from the laser that is reflected from the sample under test and the light from the laser that is reflected from the reference element; and
  an analyzer coupled to the optical detector to separate spectra contained in the spectrum composite into a plurality of spectral representations comprising at least one Raman spectral representation and at least one non-Raman spectral representation.

12. The apparatus of claim 11, wherein
the analyzer is adapted to process the Raman spectral measurements to generate a representation of a Raman spectrum.

13. A method comprising:
  concurrently communicating light from a laser to a sample under test and to a reference element;
  concurrently communicating light reflected from the sample under test to a detector and light reflected from the reference element to the detector with a dichroic material disc surrounded by a specular reflector;
  acquiring a plurality of spectral measurements of the sample under test under varying optical conditions by varying a power of the laser used to acquire the plurality of spectral measurements, one of the plurality of spectral measurements comprising a spectrum composite based upon concurrent receipt of light reflected from the reference element and light reflected from the sample under test; and
  processing the measurements, including the spectrum composite, to discriminate Raman spectra from non-Raman spectra in the spectrum composite to generate a spectral representation based upon the plurality of spectral measurements of the sample under test under the at least one varying optical condition, the spectral representation including the Raman spectra and excluding the non-Raman spectra.

14. The method of claim 13, further comprising varying the wavelength of incident radiation to the sample under test, wherein acquiring the measurements comprises acquiring the measurements for different excitation wavelengths.

15. The method of claim 13, further comprising:
  based at least in part on a result of the processing, performing at least one of detecting at least one analyte of interest and identifying the at least one analyte of interest.

16. The method of claim 13, wherein the discriminating of the Raman spectra from the non-Raman spectra in the spectrum composite comprises identifying Raman spectrum based upon wavelength shifts between the spectrum composite and a second spectrum composite.

* * * * *